(12) United States Patent
Jackson et al.

(10) Patent No.: US 10,620,174 B2
(45) Date of Patent: Apr. 14, 2020

(54) METHOD FOR IMPROVING ACCURACY OF SENSOR OUTPUTS FOR MEASURING NOX, AND SYSTEM AND APPARATUS FOR SAME

(71) Applicant: Cummins Inc., Columbus, IN (US)

(72) Inventors: Prabhu Jackson, Columbus, IN (US); Paul Daniel Borisuk, Nashville, IN (US)

(73) Assignee: Cummins Inc., Columbus, IN (US)

( * ) Notice: Subject to any disclaimer, the term of this patent is extended or adjusted under 35 U.S.C. 154(b) by 72 days.

(21) Appl. No.: 15/877,654

(22) Filed: Jan. 23, 2018

(65) Prior Publication Data

US 2019/0227043 A1      Jul. 25, 2019

(51) Int. Cl.

| F01N 13/00 | (2010.01) |
|---|---|
| F01N 11/00 | (2006.01) |
| F02D 41/14 | (2006.01) |
| G01N 33/00 | (2006.01) |
| G01M 15/10 | (2006.01) |
| F01N 3/20 | (2006.01) |

(52) U.S. Cl.
CPC ........... *G01N 33/007* (2013.01); *F01N 11/00* (2013.01); *F01N 13/008* (2013.01); *F02D 41/146* (2013.01); *G01M 15/102* (2013.01); *G01N 33/0037* (2013.01); *G01N 33/0073* (2013.01); *F01N 3/2066* (2013.01); *F01N 2560/026* (2013.01); *F01N 2570/14* (2013.01)

(58) Field of Classification Search
CPC .. F01N 11/00; F01N 13/008; F01N 2560/026; F02D 41/146; F02D 41/222
See application file for complete search history.

(56) References Cited

U.S. PATENT DOCUMENTS

| 7,788,902 B2 | 9/2010 | Tsumagari |
|---|---|---|
| 8,168,060 B2 | 5/2012 | Ding et al. |
| 8,281,572 B2* | 10/2012 | Chi .................. F01N 3/106 60/286 |
| 8,327,620 B2 | 12/2012 | Van Nieuwstadt et al. |
| 8,474,242 B2 | 7/2013 | Andrews et al. |
| 2007/0251224 A1* | 11/2007 | Andrews .................. F01N 11/00 60/301 |
| 2008/0092522 A1* | 4/2008 | Tsumagari ......... B01D 53/9409 60/274 |

(Continued)

FOREIGN PATENT DOCUMENTS

| DE | 10309422 | 9/2004 |
|---|---|---|
| EP | 1434049 | 6/2004 |

*Primary Examiner* — Audrey K Bradley
(74) *Attorney, Agent, or Firm* — Taft Stettinius & Hollister LLP

(57) ABSTRACT

A method, system, and apparatus are provided for improving accuracy of sensor readings reflecting measurements of at least one constituent in an engine exhaust. The sensor measurement is corrected or compensated for by applying to a gain correction factor to the reported sensor measurement. The gain correction factor is developed by determination of prior test sensor readings correlated with discrete sensor age levels, and with constituent concentrations to which those test sensors are exposed. By applying the determined gain correction factor to change the sensor's reported measurements, bias may be reduced and a more accurate measure of actual constituent levels is provided.

20 Claims, 6 Drawing Sheets

(56) References Cited

U.S. PATENT DOCUMENTS

2009/0288469 A1* 11/2009 Ding ................ G01N 27/4175
73/1.06
2016/0103095 A1   4/2016 Surnilla et al.

* cited by examiner

| NOx Reading (ppm) | Gain Correction Factor (G): | | | | | | | | | | |
|---|---|---|---|---|---|---|---|---|---|---|---|
| 1800 | 1.0 | 1.0 | 1.0 | 1.0 | 1.02 | 1.02 | 1.04 | 1.04 | 1.05 | 1.06 | 1.06 |
| 1600 | 1.0 | 1.0 | 1.0 | 1.0 | 1.02 | 1.02 | 1.04 | 1.04 | 1.05 | 1.06 | 1.06 |
| 1400 | 1.0 | 1.0 | 1.0 | 1.0 | 1.02 | 1.02 | 1.04 | 1.04 | 1.05 | 1.06 | 1.06 |
| 1200 | 1.0 | 1.0 | 1.0 | 1.0 | 1.02 | 1.02 | 1.04 | 1.04 | 1.05 | 1.06 | 1.06 |
| 1000 | 1.0 | 1.0 | 1.0 | 1.0 | 1.02 | 1.02 | 1.04 | 1.04 | 1.05 | 1.04 | 1.04 |
| 800 | 1.0 | 1.0 | 1.0 | 1.0 | 1.01 | 1.01 | 1.02 | 1.02 | 1.03 | 1.04 | 1.04 |
| 600 | 1.0 | 1.0 | 1.0 | 1.0 | 1.01 | 1.01 | 1.02 | 1.02 | 1.03 | 1.04 | 1.04 |
| 400 | 1.0 | 1.0 | 1.0 | 1.0 | 1.01 | 1.01 | 1.02 | 1.02 | 1.03 | 1.04 | 1.04 |
| 200 | 1.0 | 1.0 | 1.0 | 1.0 | 1.01 | 1.01 | 1.02 | 1.02 | 1.03 | 1.04 | 1.04 |
| 0 | 1.0 | 1.0 | 1.0 | 1.0 | 1.01 | 1.01 | 1.02 | 1.02 | 1.03 | 1.06 | 1.06 |
| | 0 | 1000 | 2000 | 3000 | 4000 | 5000 | 6000 | 7000 | 8000 | 9000 | 10000 |
| | Sensor Operational Age (hours) | | | | | | | | | | |

*Fig. 6*

METHOD FOR IMPROVING ACCURACY OF SENSOR OUTPUTS FOR MEASURING NOX, AND SYSTEM AND APPARATUS FOR SAME

FIELD OF THE INVENTION

The present invention relates generally to aftertreatment systems and more specifically to sensing emissions of from an internal combustion engine.

BACKGROUND

In view of increasingly stringent regulation of emissions, there is an increasing need for better closed loop control of pollutants emitted in exhaust produced by operation in an engine, and for improvements in on board diagnostics (OBD) assessing the level of the emissions. One pollutant is NOx, and many engine systems utilize a NOx sensor mounted in the exhaust system to measure the amount of NOx concentration in the exhaust, and communicate the amount of NOx to the control system of the engine system. During the useful life of a typical NOx sensor, gradual fouling of the sensor's catalytic material, as well as other conditions associated with increasing age of the sensor, may cause a decrease in the accuracy of the measurements made by the sensor, and so the actual NOx concentration in the exhaust is different from the NOx concentration reported by the sensor. Systems and methods have been developed for compensating for the change in sensitivity of the NOx sensor based on age of the sensor. However, improvements are still needed in the development of compensation factors that reduce bias resulting from aging of sensors.

SUMMARY

A method, system, and apparatus for improving accuracy of sensor measurements of one or more constituent levels in an exhaust from an engine are disclosed. The method and system comprise correction of measurements taken by the sensor, by applying to the reported sensor reading a gain correction factor developed by determination of prior actual sensor readings correlated with discrete sensor age levels, and constituent concentrations to which those sensors are exposed. The gain correction factor is determined by using test results from exposing a plurality of equivalent sensors of different service ages to different constituent levels. By applying the determined gain correction factor to the sensor's reported measurements, the method, system, and apparatus change the measurements reported by the sensor based on the sensitivity of the sensor to different constituent levels at the service age of the sensor. As a result, bias may be reduced and a more accurate measure of actual constituent levels is provided.

BRIEF DESCRIPTION OF THE DRAWINGS

FIG. 6 is a table illustrating representative gain correction factors determined in accord with the present disclosure.

DETAILED DESCRIPTION

The present invention relates generally to engines and more specifically to sensing one or more constituent levels in the exhaust from of such engines. The following description is presented to enable one of ordinary skill in the art to make and use the invention and is provided in the context of a patent application and its requirements. Various modifications to the illustrated embodiments and the generic principles and features described herein will be readily apparent to those skilled in the art. Thus, the present invention is not intended to be limited to the embodiments shown, but is to be accorded the widest scope consistent with the principles and features described herein.

Internal combustion engine systems such as diesel systems may utilize a NOx sensor mounted in the exhaust system to measure the amount of NOx concentration or other constituent level in the exhaust. Over the service life of a typical NOx sensor, a gradual increase in the fouling of the sensor's catalytic material, as well as other conditions associated with increasing age of the sensor, may cause a decrease in the sensitivity of the sensor, and accordingly, a decrease in the accuracy level of the measurements made by the sensor. This decrease in accuracy is represented in FIG. 1, a diagram which shows the loss of sensitivity resulting in bias in the sensor readings, thereby causing the sensor to provide less accurate information as it ages.

Figure 1:
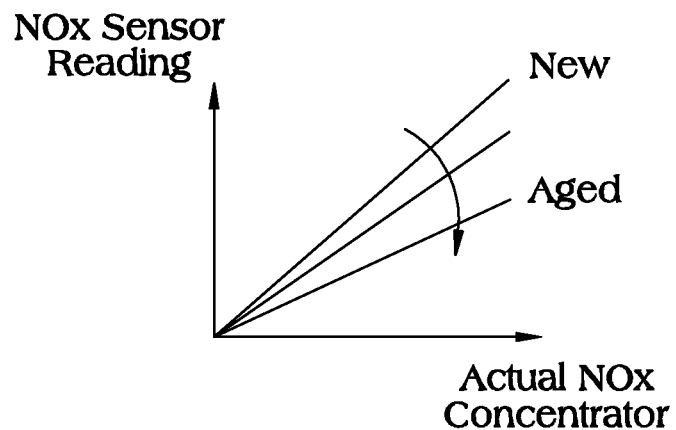
FIG. 1 is a diagram showing loss of sensor sensitivity over time.

In response to the decline in sensitivity as illustrated in FIG. 1, efforts have been made to apply compensation factors to sensor readings in order to adjust measurements by the sensor to correct for age-related bias. For example, the age of the sensor (in terms of number of hours of operation) has been measured by an internal clock system or module in a NOx sensor processing module. A gain correction factor has been applied to sensor measurements as a function of such sensor age. However, an aged sensor curve as schematically represented in FIG. 1 may vary considerably based on sensor model and the conditions in the exhaust gas. Although the diagram in FIG. 1 indicates lowered readings reported by an aged sensor, there is not always a direct association. Some readings provided by an aging sensor may actually be accurate, or may be over-reporting NOx concentration levels, in certain conditions.

The inventors herein have developed a system, method, and apparatus for improving age-related bias correction and overcoming the shortcomings of an estimation system based only on sensor age. The system, method and apparatus preferably include recordal of actual sensor outputs of particular models of sensors at discrete points in operational age when exposed to a range of known NOx concentrations. The system and method thus provide a data set reflecting sensor bias in a given model at given ages under a range of NOx concentrations. The data set is used to determine gain correction factors that account for chronological age of a sensor as well as the drift that occurs at different points in the operational life of the particular model of sensor. Applying the resulting gain correction factors, it becomes possible to correct for drift in raw NOx measurements reported by a sensor, and thus to more accurately represent actual NOx concentrations in the exhaust gas. The method, system, and apparatus may be employed in any prime mover system having an exhaust stream, and may be employed in a diesel engine system or other types of engine systems. The method, system and apparatus may also have application to sensors other than NOx sensors, and to one or more constituents in the exhaust produced by the engine other than NOx.

Figure 2:
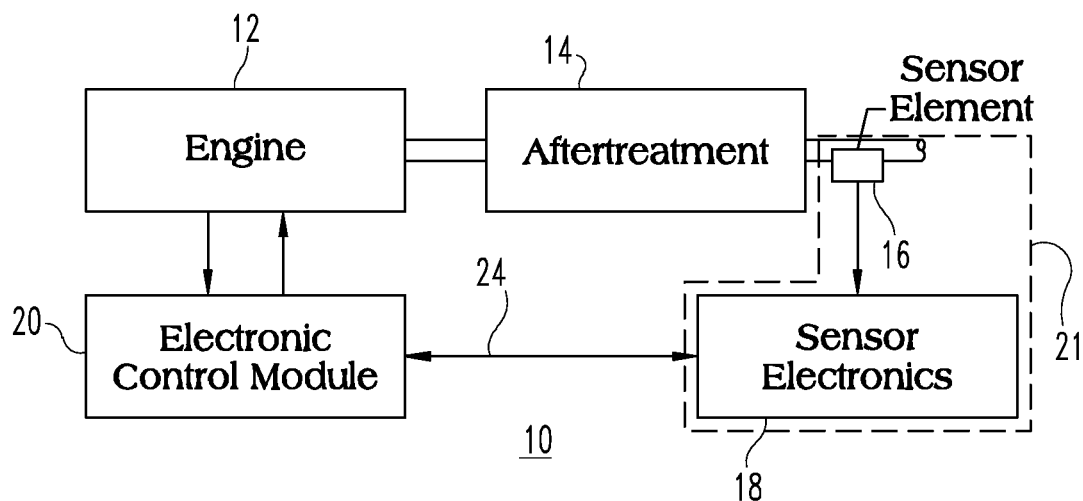
FIG. 2 is a simplified block diagram of a first embodiment of an engine system.

FIG. 2 is a simple block diagram of a first embodiment of an engine system 10. The engine system 10 comprises an engine 12 coupled to an aftertreatment unit 14. Operation of the engine 12 is controlled by an electronic control module (ECM) 20.

As seen in FIG. 2, The ECM 20 communicates with a sensor system 21 to detect and control exhaust emissions. The sensor system 21 includes sensor electronics 18 and a sensor element 16. The sensor element 16 is mounted in the system-out exhaust stream, so that it can measure the amount of NOx concentration in the exhaust produced by the system. Information from the sensor element 16 can be provided to the sensor electronics 18 via the controller area network (CAN) bus, SAE-J-1939 bus 24 or any other suitable connection. The sensor electronics 18 sends information to and receives information from the electronic control module (ECM) 20.

The sensor electronics 18 may, for example, along with other functions, provide an onboard diagnosis (OBD) system. The OBD system contained within the sensor electronics performs at least three functions based on the data received from the sensor element 16: (1) detects short circuits and open wires, and delivers an error message on the data link to the electronic control module; (2) performs analysis of the exhaust gas aftertreatment system to recognize static and dynamic sensor failures; and (3) detects NOx and/or other constituent levels in the exhaust.

Figure 3:
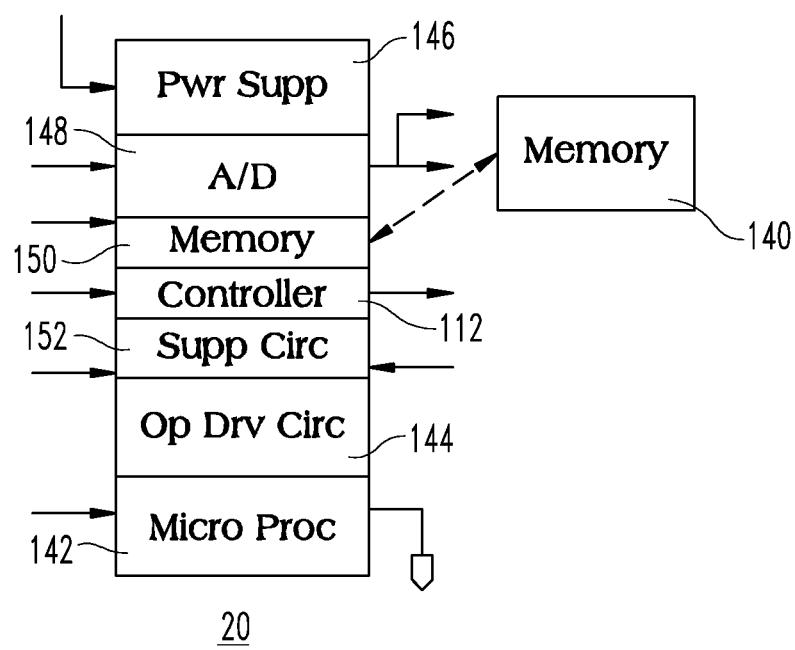
FIG. 3 is a diagram of an electronic control module of an engine system.

FIG. 3 is a block diagram of an ECM 20 as illustrated in FIG. 2. Referring to FIG. 3, the electronics control module 20 includes as its central component a controller 112.

Controller 112 may be a microcomputer including a microprocessor portion 142, an output driver portion 144 including output interface circuitry, a power supply portion 146, an analog-to-digital converter portion 148, a memory portion 150 and a supporting circuitry portion 152. In certain embodiments, the controller 112 may form a portion of a processing subsystem including one or more computing devices having memory, processing, and communication hardware. The controller 112 may be a single device or a distributed device, and the functions of the controller 112 may be performed by hardware or software instructions encoded on a computer readable medium. The controller 112 may be included within, partially included within, or completely separated from an engine controller (not shown). The controller 112 is in communication with any sensor or actuator throughout the system as disclosed herein, including through direct communication, communication over a datalink, and/or through communication with other controllers or portions of the processing subsystem that provide sensor and/or actuator information to the controller 112. The controller 112 includes stored data values, constants, and functions, as well as operating instructions stored on computer readable medium. Any of the operations of exemplary procedures described herein may be performed at least partially by the controller 112. Other groupings that execute similar overall operations are understood within the scope of the present application. Modules may be implemented in hardware and/or on one or more computer readable media, and modules may be distributed across various hardware or computer implemented components. More specific descriptions of certain embodiments of controller operations are discussed herein below.

In an embodiment, the microprocessor portion 142 of controller 112 runs control routines and manages the overall operation of the system 10. The microprocessor portion 142 may contain the analog-to-digital converter portion 148 for converting analog sensor signals to digital signals for further processing by the microprocessor portion 142.

The memory portion 150 of controller 112 may include ROM, RAM, RPROM, EEPROM, Flash PROM and any other reusable type of memory known to those skilled in the art. The memory portion 150 may be further supplemented by memory 140 connected thereto as shown by a dashed-line connection. Memory 140 may include any of the memory features described with respect to memory portion 150. Memory 140 may also be used to supplant memory portion 150 if controller 112 lacks a memory portion 150 or if memory portion 150 provides inadequate storage. Finally, the microprocessor portion 142 may include sufficient memory (including ROM and RAM) to obviate the need for memory portion 150 and/or supplemental memory 140.

The power supply portion 146 of controller 112 receives electrical power from the battery 124 (not shown) through key switch 122 (not shown) when key switch 122 is in the "on" position, and supplies electrical power to the various controller portions as well as supporting circuitry which may be added to the system 10. The output driver portion 144 of controller 112 supplies power output signals capable of driving relays, switches and the like.

The supporting circuitry portion 152 may include, for example, interface circuitry for conditioning input signals, a UART, load dump and electrostatic discharge (ESD) protection circuitry, buffer circuitry and other circuitry commonly associated with microcomputers.

Figure 4A:
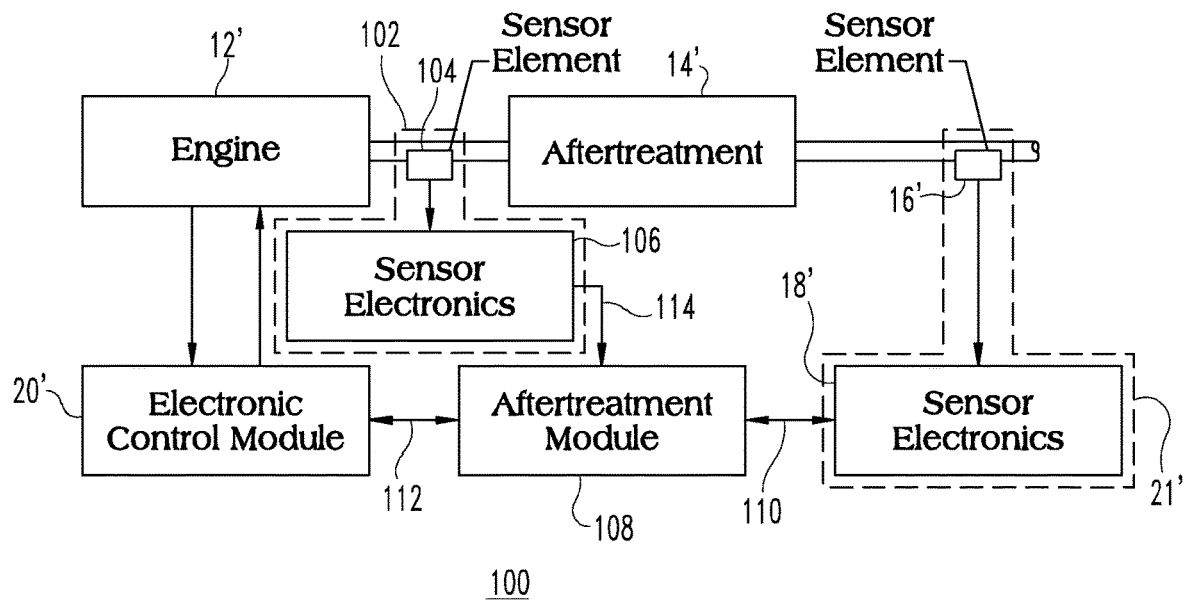
FIG. 4A is a simplified block diagram of a second embodiment of an engine system.

FIG. 4A is a block diagram of a second embodiment of an engine system 100. In addition to elements corresponding to those described in the first embodiment in FIG. 2, including engine 12', aftertreatment system 14', and sensor element 16', this second embodiment includes a second sensor system 102 and includes an aftertreatment module (ATM) 108 and sensor electronics 106. The sensor system 102 also includes a sensor element 104. The aftertreatment module 108 can be coupled to sensor system 21', sensor system 102 and electronic control module 20' via the CAN buses (Europe), SAE-J-1939 buses (US) 110, 112 and 114, or other suitable connection.

Figure 4B:
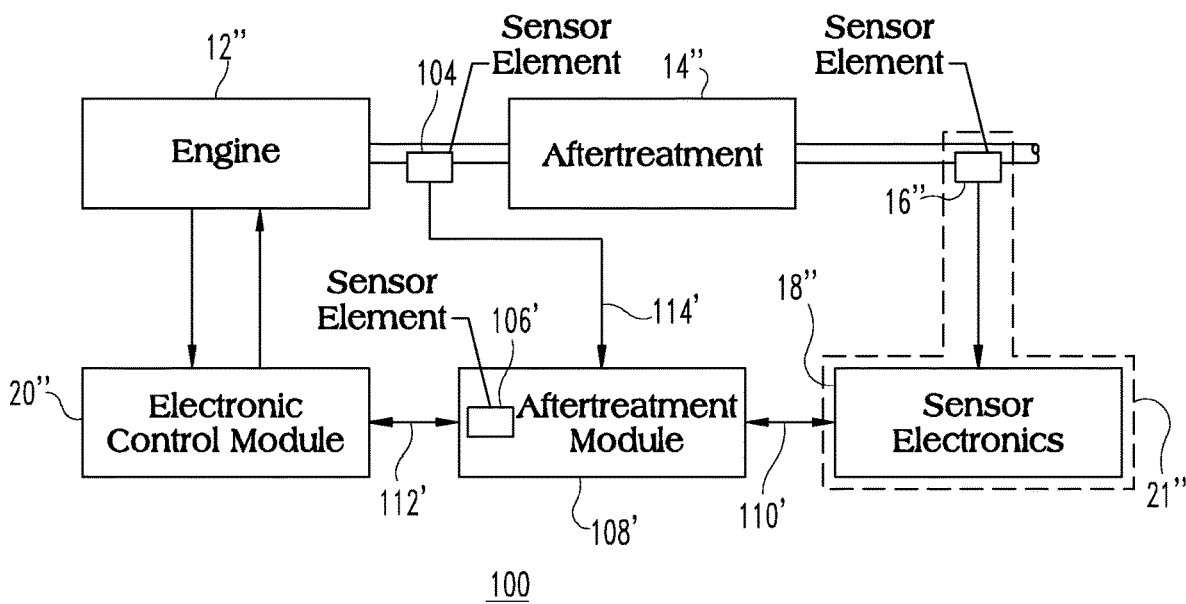
FIG. 4B is a simplified block diagram of a third embodiment of an engine system.

FIG. 4B is a block diagram of a third embodiment of an engine system. The system 100 includes elements corresponding to those described in the first embodiment in FIG. 2, including engine 12", aftertreatment system 14", sensor element 16", ECM 20", sensor system 21", sensor electronics 18", buses 110", 112", and 114", and second sensor element 104". The system 100 works substantially the same as system 100 described in FIG. 4A except that the sensor electronics 106' is integrated within the ATM 108'. By so doing, the circuitry utilized on the engine may be substantially simplified.

The aftertreatment module 108, 108' may perform the following functions: receives and processes the two NOx sensor inputs; computes current efficiency of the SCR catalyst; computes the current maximum efficiency of the catalytic convertor; computes the desired urea dosing rate; controls the urea doser; performs sensor diagnostics; performs urea doser diagnostics; communicates with the ECM (information such as system status, diagnostics, control parameters); computes the ammonia storage based upon current conditions and adaptive storage model; and/or calculates the sensor correction based upon engine hours and the total accumulated NOx.

Figure 5:
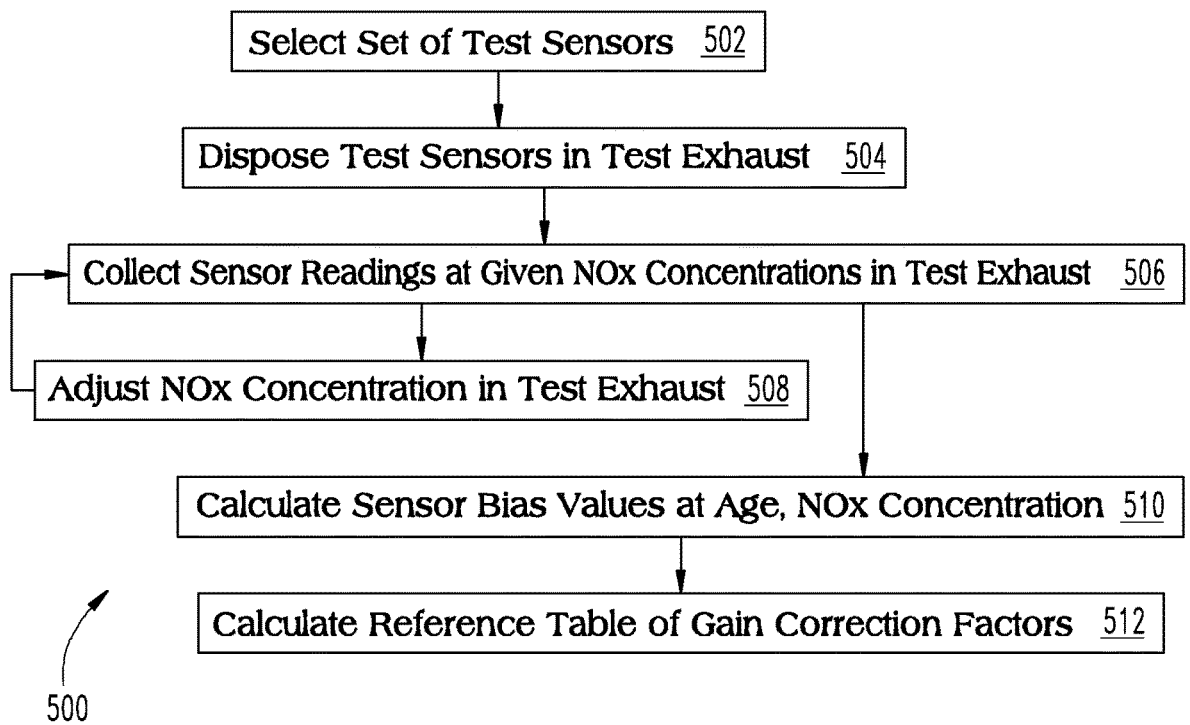
FIG. 5 is a flow chart showing operations for establishing a set of gain correction factors for improving accuracy of sensor readings.

FIG. 5 is a flow chart depicting a system or method 500 for establishing a table of gain correction factors to improve sensor accuracy in accord with the present disclosure. The system or method may be applied in an apparatus of the present disclosure. The establishment of the table includes a first operation 502 of selecting a plurality or set of test sensors. The plurality of test sensors may be a group of equivalent sensors, such as a group comprised of sensors made by the same manufacturer, and/or being the same model or type, and/or being manufactured in the same model year or lot. The plurality of test sensors may be a group of NOx sensors of a particular model typically used in diesel engines, but other sensor types are also contemplated.

Members of the model group are selected such that different operational ages are represented within the model group. The operational age, or service age, is based upon an aggregate amount of time that the sensor has been operated. The test sensors of the model group are selected such that the test sensors have different operational ages within particular age ranges. The age ranges may be selected to be within increments of a normal expected operational life for that particular model of sensor. For example, a first set of test sensors within the model group may constitute an age category having operational ages between zero to 3,000 hours, and second through nth sets of sensors may, within a model group, constitute an age category having respective operational ages within additional 3,000 increments thereafter. As shown in the example of the table of FIG. 7, a sensor model may have an expected operational life of about 36,000 hours, and members of the model group are categorized according to their respective operational age ranges, in 3,000 hour increments.

Sufficient numbers of group members within each age category are selected for the sample, so that a data set having statistical significance is developed, and variability in the data set may be maintained at an acceptably low level, as to each age category. It is also contemplated that sensor tests may be repeated a sufficient number of times to aid in achieving an acceptably low level of variability in the data set. It is contemplated that the selection process above may be applied to sets of test sensors of a number of different models, so that a separate data set may be developed for each one of a number of typical sensor models.

An operation 504 in the system or method 500 includes disposing the selected test sensors in test exhaust conditions. In one embodiment, the operation 504 may include disposing the test sensors in an exhaust under controlled conditions, such as in a test chamber or test apparatus containing test exhaust. The controlled conditions may include parameters such as exhaust temperature, streaming rate, pressure level, and exhaust gas content. A controlled condition of the test exhaust content may include control of concentration levels of one or more constituents such as NOx present in the test exhaust (may be measured as parts per million (ppm)).

At operation 506, the groups of sensors are operated in the test exhaust conditions, the conditions including a known, given concentration of NOx or other constituent present in the test exhaust gas, and sensor readings, or measurements, are detected. The detected sensor readings are recorded and collected. For each group of test sensors having an operational age within a given range, the collection of the readings establishes a data set such that a mean NOx gas content reading may be calculated and recorded for the group of sensors in each age category exposed to the given NOx concentration. In an embodiment, the NOx gas content readings may be averaged to yield a mean value for the group of equivalent sensors, but other applicable sampling calculations may be applied, such as linear, exponential, logarithmic, or other calculation means, to provide an estimated data set.

An operation 508 is conducted in which the test exhaust conditions are adjusted. In one embodiment, the concentration level of the NOx gas present in the test exhaust gas is increased or decreased so that another iteration of the collection step at operation 506 is repeated at a different NOx concentration level. Via additional iterations of adjusting NOx concentration at operation 508, and then detecting, collecting, and recording test sensor readings at operation 506, a separate data set is developed. This separate data set is specific to the actual NOx concentration level at which the readings were collected, and specifically pertains to each group of test sensors having a given operational age.

At operation 510, the data sets developed after iterations of operations 506 and 508 are used to calculate sensor bias values. A sensor bias value pertaining to sensors in a given age category may be calculated by comparing a mean of the test sensor readings collected from all equivalent sensors of the age group to the actual NOx concentrations in the controlled exhaust gas. A sensor bias value thus may be calculated and recorded for each age group that is specific to each actual NOx concentration level to which the group has been exposed. The recorded bias values may be communicated to and stored in the ECM 20 or one or more other components of the system.

At operation 512, the stored bias value for each such group of equivalent sensors at each NOx concentration level may be used to calculate a gain correction factor G for that group. The gain correction factor calculation may be represented by the equation:

$$G = f(NOx \text{ sensor reading, sensor age in operating hours}) \quad \text{(Equation 1)}$$

In one embodiment, the calculated gain correction factors G may each be interpolated to fall within a range of 0.500 to 1.500, with a precision of 0.001, and are expressed with no units of measurement. A default factor of 1.000 may be applied as the gain correction factor G in instances where bias was not found in the test sensor group, or the data set was insufficient or otherwise incompetent to establish a gain correction factor G for that group.

The method and system 500 thus develop a set of gain correction factors G for use in tables, such as the example table 600 shown in FIG. 6. In the exemplary table 600 of FIG. 6, a set of ranges of operational ages of sensors (in increments of 3,000 hours of operation up to a typical expected sensor life of 36,000 hours) is selected for the gain correction factor table. FIG. 6 also reflects selection of a set of ranges of typical NOx concentration levels found in the exhaust, in this example, a set of ranges within 1,000 ppm increments, up to an upper reading of 10,000 ppm. The factors are interpolated between the breakpoints of the respective incremental ranges in the operational hours axis and the NOx readings ppm axis of this example table 600.

As noted above, the underlying test sensor data may be collected for a plurality of different sensor types or models. In such instance, a separate table 600 as in FIG. 6 may be developed that pertains to each model so tested. As may be appreciated from the sample factors G shown in FIG. 6, the improved method, system, and apparatus disclosed herein allow for improvement in prior compensation methods, in that a two-factor correlation to test data is provided, in contrast to prior systems providing a linear data curve representing only age. This approach will more realistically predict the performance of a given sensor model over time, accounting not only for the sensor's age, but also for that particular sensor's expected performance when exposed to particular NOx concentrations at particular points during the course of the sensor's operational life.

The gain correction factors G as exemplified in FIG. 6 are to be applied by the ECM 20 to correct for the amount of drift exhibited by a particular type of sensor of a given age when exposed to a given NOx concentration level. One or more tables 600 may be stored in the memory portion 150 of the ECM 20, or one or more modules thereof. Such stored tables may be referenced in making the correction during operation of the engine 12, 12', or engine system 10, 100, such that the ECM 20 may determine values and generate and communicate command signals for the control of engine operation based on the correction.

Figure 7:
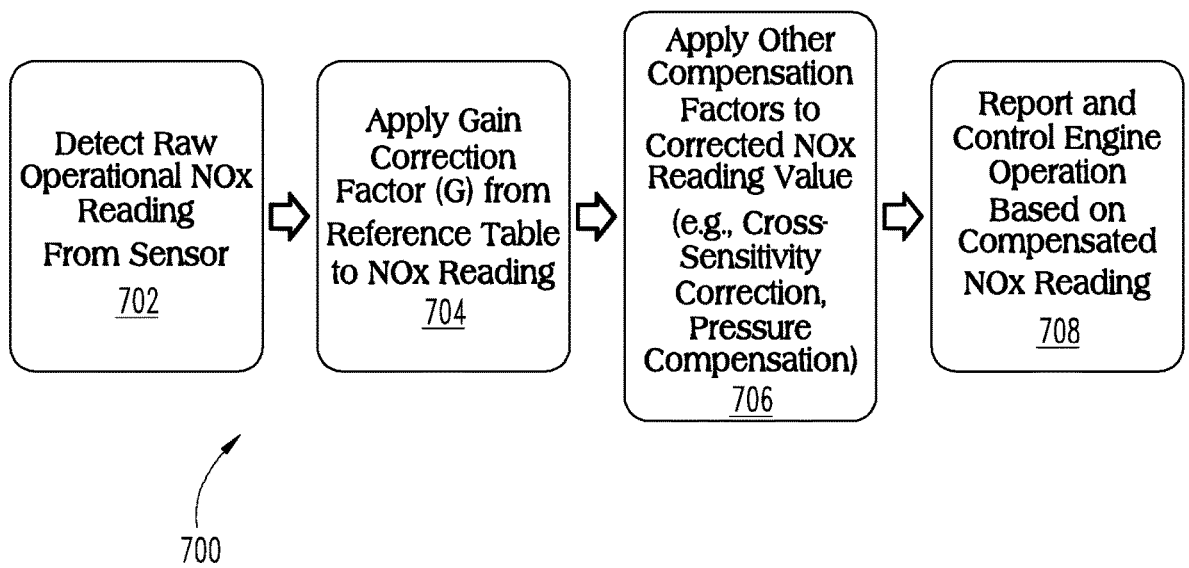
FIG. 7 is a flow chart showing application of gain correction factors to sensor measurements in order to improve accuracy of the sensor.

As seen in FIG. 7, a method and system 700 are disclosed for application of the gain correction factors G of table 600 in reporting on engine performance and in controlling operation of the engine 12, 12' or engine system 10, 100. In operation 702, the sensor element 16 mounted in the exhaust detects the level of NOx concentration in the exhaust, and is reported by the sensor element 16 as a measured or detected NOx level. The measured or detected NOx level from the sensor element 16, $NOx_{sensor}$, is provided to the sensor electronics 18 via the provided communication means such as bus 24. The detected NOx concentration value $NOx_{sensor}$ can be the raw NOx value as detected by the sensor element 16, prior to any other compensation factors being applied to the value by the ECM 20 or other processing units of the sensor 16 or the system 10, 100.

At operation 704, the applicable gain correction factor G is selected from table 600 by the ECM 20, or one or more of its components or modules, based on sensor operational age and the raw NOx reading, $NOx_{sensor}$, supplied by the sensor 16. The operation 704 includes obtaining the sensor operational age, which typically is recorded by an internal sensor clock program existing in a processing unit of the sensor 16, or within a NOx sensor processing module of the ECM or other component thereof. In one embodiment, periodically the ECM 20 will query the sensor 16 via the sensor electronics via a CAN (controller area network) link to receive sensor operating hours. Having the sensor keep track of its own time and communicating that information to the ECM 20 eliminates the potential algorithm problem if the sensor is replaced without the ECM's knowledge.

Further at operation 704, based on the determined operational age and $NOx_{sensor}$, the raw NOx reading supplied by the sensor, the table 600 stored in the memory portion 15 of the controller 112 is referenced by the ECM 20 or its modules. The applicable gain correction factor G is chosen from the table 600, and applied to the raw NOx reading in a calculation represented by: $NOx_{actual} = NOx_{sensor} \times G$, wherein $NOx_{actual}$ is the actual NOx constituent amount in the exhaust, $NOx_{sensor}$ is the NOx constituent amount in the exhaust as measured by the sensor, and G is the beforementioned gain correction factor G, which may be determined from the table in FIG. 6. The ECM 20 is thus configured to change the measurement made by the sensor based on sensitivity of the sensor to different constituent levels at a service age of the sensor.

At optional operation 706, the $NOx_{actual}$, representing a corrected emissions reading, may be further adjusted by applying other compensation factors to the corrected NOx reading value to arrive at a compensated NOx reading value. For example, modules of the sensor elements 16, 16', sensor electronics 18, ECM 20, and/or the aftertreatment module 108, 108' may be adapted to apply such additional adjustment factors. The adjustment factors may include adjustments for sources of bias other than aging/actual NOx levels as addressed in table 600; the former may include such factors as $NO/NO_2$ ratios in the exhaust, pressure conditions affecting the sensor, cross-sensitivities affecting pressure readings, and other known impacts on sensor readings. In an embodiment, the raw NOx reading $NOx_{sensor}$ supplied by the sensor 16 is corrected by application of the correction factor G prior to such additional optional adjustments, to aid in arriving at an accurate reading.

At operation 708, the compensated NOx reading value ($NOx_{actual}$), which may have been further adjusted in optional operation 706, is reported to and recorded in the memory elements of the ECM 20. The recording in the memory elements is provided for the purpose of reporting on engine performance and emissions values. Also at operation 708, the corrected NOx reading value may be used to control or adjust engine operation by means of the ECM 20 providing operational commands to the engine 12, 12' or system 10, 100 based on the compensated NOx reading value.

As the result, NOx emissions may be more accurately reported due to correction of the reading values or outputs reported as the measurements made by the sensors. The change of the measurement based on sensitivity of the sensor to different constituent levels at the service age of the respective sensor improves the accuracy of the assessment of actual NOx emissions. Also, engine operation may be more efficiently and economically controlled by utilizing the method, system and apparatus herein disclosed, which may be applied to control or adjust engine operation to reduce NOx emissions, to improve fuel economy by controlling or adjusting engine operation in response to the NOx emission levels detected, and/or to achieve other engine operational conditions which may be more effectively accomplished due the increased accuracy in emission readings provided by the present disclosure. Moreover, use of the systems, methods and/or apparatus of the present disclosure may provide for improved control of costs associated with replacement of sensors, such as by avoiding premature replacement of sensors that continue to function well, despite increasing operational age.

As may be appreciated by contrasting FIG. 2 on the one hand with FIGS. 4A and 4B on the other hand, the method, system, and apparatus herein disclosed may be applied to a number of sensors, including, for example, a first sensor disposed in engine-out exhaust, a second sensor disposed in system-out exhaust, or a plurality of sensor disposed in both engine-out and the system-out exhaust. For example, as illustrated in FIG. 4A, the raw operational sensor outputs from the sensor disposed to detect and measure constituent levels in the engine-out exhaust stream, namely sensor element 104, may be corrected using the operations in FIG. 5. Similarly, as illustrated in FIG. 4A, the raw operational sensor outputs from the sensor disposed to detect and measure constituent levels in the system-out exhaust stream, namely sensor element 16', may be corrected using the operations in FIG. 5. Then the operations in FIG. 7 may be applied to the corrected values from each of the two sensors. In this manner, each sensor may have corrective factors applied to its readings that are related to the particular model and age of each one of the sensors, correlated to the NOx concentration conditions separately encountered by each of the two sensors 16' and 104. In this respect, in the preceding discussion, reference to one of the sensors or sensor systems should also be taken to apply to other sensors or sensor systems as shown in the various views of the drawings herein. Applying the method, system and apparatus having more than one sensor provides the benefit of allowing for comparison between the measurements and corrected measurements to aid in detecting and diagnosing problems with engine operations along the exhaust system.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims. In reading the claims, it is intended that when words such as "a," "an," or "at least one," are used there is no intention to limit the claim to only one item unless specifically stated to the contrary in the claim.

What is claimed is:

1. A method for improving sensor accuracy for measuring at least one constituent in an exhaust produced by an engine, comprising:
    measuring the at least one constituent in the exhaust using a sensor; and
    changing the measurement based on a sensitivity of the sensor to different constituent levels at an operational age of the sensor, the change in the measurement being based on a gain correction factor determined from a reading of the sensor and the operational age of the sensor, wherein for the same operational age of the sensor, the gain correction, factor varies based on the reading of the sensor.

2. The method of claim 1, wherein the changing is implemented in accordance with the following equation:

$$NOx_{actual} = NOx_{sensor} \times G,$$

wherein $NOx_{actual}$ comprises an actual NOx constituent level,
$NOx_{sensor}$ comprises a NOx constituent level as measured by the sensor, and
G comprises the gain correction factor.

3. The method of claim 2, wherein the operational age is based upon, an aggregate amount of time that the sensor has been operated.

4. The method of claim 2, wherein the gain correction factor is determined by using test results from exposing a plurality of equivalent sensors of different operational ages to different constituent levels.

5. The method of claim 4, wherein the test results comprise a bias value for a group of the equivalent sensors having a given operational age when exposed to a given constituent level.

6. The method of claim 5, wherein the bias value is a mean value for the group of equivalent sensors.

7. A system, comprising:
    a control module operatively connected to an engine, and operatively connected to a sensor system for sensing at least one constituent in an exhaust from the engine, wherein
    the sensor system comprises a sensor; and
    the control module is configured to change a measurement made by the sensor based on sensitivity of the sensor to different constituent levels at an operational age of the sensor, the change in the measurement being based on a gain correction factor determined from a reading of the sensor and the operational age of the sensor, wherein for the same operational age of the sensor, the gab correction factor varies based on the reading of the sensor.

8. The system of claim 7, wherein the sensor is a first sensor positioned to detect engine-out constituent levels in the exhaust from the engine.

9. The system of claim 8, wherein the sensor system comprises a second sensor positioned to detect system-out constituent levels from an aftertreatment system of the engine, and the control module is configured to change the measurement made by the respective sensor based on sensitivity of the respective sensor to different constituent levels at the operational age of the respective sensor.

10. The system of claim 7, wherein the change in the measurement is implemented in accordance with the following equation:

$$NOx_{actual} = NOx_{sensor} \times G,$$

wherein $NOx_{actual}$ comprises an actual NOx constituent level,
$NOx_{sensor}$ comprises a NOx constituent level as measured by the sensor, and
G comprises the gain correction factor.

11. The system of claim 10, wherein the gain correction factor is determined by using test results from exposing a plurality of equivalent sensors of different operational ages to different constituent levels.

12. The system of claim 11, wherein the test results comprise a bias value for a group of the equivalent sensors having a given operational age when exposed to a given constituent level.

13. The system of claim 12, wherein the bias value is a mean value for the group of equivalent sensors.

14. An apparatus, comprising:
    a sensor disposed to detect at least one constituent in an exhaust from an engine; and
    a control module operatively connected to the engine and the sensor, wherein
    the control module is configured to change a measurement made by the sensor based on sensitivity of the sensor to different constituent levels in the exhaust at an operational age of the sensor, the change in the measurement being based on a gain correction factor determined from reading of the sensor and the operational age of the sensor, wherein for the same operational age of the sensor, the gain correction factor varies based on the reading of the sensor.

15. The apparatus of claim 14, wherein the operational age is based upon an aggregate amount of time that the sensor has been operated.

16. The apparatus of claim 14, wherein the change in measurement is implemented in accordance with the following equation:

$$NOx_{actual} = NOx_{sensor} \times G,$$

wherein $NOx_{actual}$ comprises an actual constituent level,
$NOx_{sensor}$ comprises a constituent level as measured by the sensor, and
G comprises the gain correction factor.

17. The apparatus of claim 16, further comprising an aftertreatment system for treating the at least one constituent from the engine.

18. The apparatus of claim 14, wherein the gain correction factor is determined by using test results from exposing a plurality of equivalent sensors of different service ages to different constituent levels.

19. The apparatus of claim 18, wherein the test results comprise a bias value for a group of the equivalent sensors having a given operational age when exposed to a given constituent level.

20. The apparatus of claim 19, wherein the bias value is a mean value for the group of equivalent sensors.

\* \* \* \* \*